(12) United States Patent
Gil et al.

(10) Patent No.: US 10,940,054 B2
(45) Date of Patent: Mar. 9, 2021

(54) DISPOSABLE DIAPER WITH INLET CUTTING PART ON SKIN CONTACT LAYER

(71) Applicants: Jun Mo Gil, John Creek, GA (US); Jin Sun Park, John Creek, GA (US)

(72) Inventors: Jun Mo Gil, John Creek, GA (US); Jin Sun Park, John Creek, GA (US)

(*) Notice: Subject to any disclaimer, the term of this patent is extended or adjusted under 35 U.S.C. 154(b) by 322 days.

(21) Appl. No.: 15/765,001

(22) PCT Filed: Oct. 21, 2015

(86) PCT No.: PCT/KR2015/011112
§ 371 (c)(1),
(2) Date: Mar. 30, 2018

(87) PCT Pub. No.: WO2017/069299
PCT Pub. Date: Apr. 27, 2017

(65) Prior Publication Data
US 2018/0271718 A1    Sep. 27, 2018

(51) Int. Cl.
*A61F 13/513* (2006.01)
*A61F 13/512* (2006.01)
(Continued)

(52) U.S. Cl.
CPC .......... *A61F 13/513* (2013.01); *A61F 13/491* (2013.01); *A61F 13/495* (2013.01);
(Continued)

(58) Field of Classification Search
CPC ............ A61F 13/495; A61F 2013/4951; A61F 2013/4955; A61F 2013/4956; A61F 2013/4958; A61F 2013/4953; A61F 13/512; A61F 13/49015; A61F 13/49019; A61F 13/491; A61F 13/496; A61F 13/513;
(Continued)

(56) References Cited

U.S. PATENT DOCUMENTS 5,171,236 A    12/1992  Dreier et al.
5,342,342 A *  8/1994  Kitaoka ............ A61F 13/49473
                                              604/385.19
(Continued)

FOREIGN PATENT DOCUMENTS

JP         11113958       4/1999
JP        2012024176      2/2012
(Continued)

OTHER PUBLICATIONS

International Search Report and Written Opinion of the International Searching Authority corresponding to International Patent Application No. PCT/KR2015/011112 dated Jul. 13, 2016 (8 pages).

*Primary Examiner* — Michele M Kidwell
(74) *Attorney, Agent, or Firm* — Myers Biqel, P.A.

(57) ABSTRACT

The present invention relates to a disposable diaper for absorbing and receiving excreted urine and feces, The diaper includes a base layer including an absorber and a cover layer positioned at an upper end of the absorber. A skin contact layer is positioned at an upper end of the base layer so as to cover the cover layer, having an inlet cutting part cut in a predetermined length such that urine and feces reach the cover layer or the absorber.

8 Claims, 5 Drawing Sheets

(51) Int. Cl.
*A61F 13/49* (2006.01)
*A61F 13/491* (2006.01)
*A61F 13/495* (2006.01)
*A61F 13/496* (2006.01)

(52) U.S. Cl.
CPC ...... *A61F 13/496* (2013.01); *A61F 13/49015* (2013.01); *A61F 13/49019* (2013.01); *A61F 13/512* (2013.01); *A61F 2013/4958* (2013.01); *A61F 2013/51355* (2013.01)

(58) Field of Classification Search
CPC ...... A61F 2013/51355; A61F 13/49001; A61F 13/49017; A61F 2013/4587
See application file for complete search history.

(56) References Cited

U.S. PATENT DOCUMENTS

| | | | |
|---|---|---|---|
| 6,248,098 B1 | 6/2001 | Sayama | |
| 6,458,114 B1 * | 10/2002 | Mishima | A61F 13/49473 604/385.101 |
| 7,666,173 B2 * | 2/2010 | Mishima | A61F 13/4915 604/385.101 |
| 8,439,885 B2 * | 5/2013 | Sakano | A61F 13/495 604/348 |
| 10,470,943 B2 * | 11/2019 | Jang | A61F 13/49466 |
| 2002/0120248 A1 * | 8/2002 | Onishi | A61F 13/49466 604/385.19 |
| 2004/0039363 A1 | 2/2004 | Sugiyama et al. | |
| 2005/0143710 A1 | 6/2005 | Van Gompel et al. | |
| 2008/0221545 A1 * | 9/2008 | Suzuki | A61F 13/49413 604/385.101 |
| 2011/0270211 A1 | 11/2011 | Roe et al. | |

FOREIGN PATENT DOCUMENTS

| | | |
|---|---|---|
| KR | 10-0263226 | 9/2000 |
| KR | 1020040067544 | 7/2004 |
| KR | 20-0365056 | 10/2004 |
| KR | 10-0945976 | 3/2010 |
| KR | 10-1106411 | 1/2012 |

* cited by examiner

DISPOSABLE DIAPER WITH INLET CUTTING PART ON SKIN CONTACT LAYER

CROSS REFERENCE TO RELATED APPLICATION

This application is a 35 U.S.C. § 371 national stage application of PCT International Application No. PCT/KR2015/011112, filed Oct. 21, 2015, the content of which is incorporated herein by reference in its entirety. The above-referenced PCT International Application was published in the Korean language as International Publication No. WO 2017/069299 A1 on Apr. 27, 2017.

TECHNICAL FIELD

The present invention relates to a disposable diaper, and more particularly to a disposable diaper for absorbing and receiving excreted urine and feces.

BACKGROUND ART

In general, disposable diapers as products which are once used and then, discarded are divided into disposable diapers for an infant or an adult, and a main function of a diaper worn by an infant or an adult with incontinence is to absorb and contain body secretions such as urine and feces.

Thus, the diaper can prevent the body secretions from dirtying or wetting clothes which a wearer wears or other products in the vicinity.

The disposable diaper which is conventionally used has a structure in which a suction sheet made of a nonwoven fabric and a waterproof sheet made of a waterproof material are laminated on both sides of an absorbent layer made of a high absorber to constitute a diaper body and an elastic body is installed on the diaper body so that a part surrounding the waist, a space between legs, and the buttocks of a wearer are brought into close contact with the wearer, and the diaper body is worn using an adhesive tape fixed to one side of the diaper body when the diaper body is worn.

However, in the case of feces, particularly, dilute feces may adhere to a part of the diaper opposed to the anus and spread to the waist and the buttocks. In this case, harmful bacteria in the feces may enter the urinary tract (especially the urinary tract of the female) and cause urinary tract infections, which may increase the risk of cystitis.

PRIOR ART DOCUMENT

Patent Document

Korean Utility Model No. 0365056 (Registration date: Oct. 6, 2004, Title: Diaper)

DETAILED DESCRIPTION OF THE INVENTION

Technical Problem

The present invention is to provide a disposable diaper which separately treats urine and feces of a wearer and reduces contact of the feces with a skin of the wearer.

The present invention is also to provide a disposable diaper which minimizes contact between the secretion inside a diaper, which is in contact with a skin and the skin of a wearer to prevent damage and disease caused by skin contamination of the wearer.

The technical objects to be achieved by the present invention are not limited to the above-mentioned technical objects.

Technical Solution

In order to achieve the object, a disposal diaper according to the present invention, which is divided into a front surface part touching the wearer's abdomen, a rear surface part touching the wearer's back, and a gap part in which the front surface part and the rear surface part extend in the lengthwise direction so as to pass between the wearer's legs, is integrally configured to include: a base layer including an absorber at an upper end thereof in the lengthwise direction on the basis of the center of the gap part, and including first elastic members on both sides in the lengthwise direction so as to encompass the wearer's legs; a cover layer positioned at an upper end of the absorber so as to cover the absorber; and a skin contact layer positioned at an upper end of the base layer so as to cover the cover layer, having an inlet cutting part cut in a predetermined length such that urine and feces easily reach the cover layer or the absorber, and having second elastic members, which come into close contact with the bottom layer skin of the wearer's buttocks in the lengthwise direction on both sides and are spaced apart from the inlet cutting part at predetermined intervals.

Specifically, the inlet cutting part is divided into a urine inlet cutting part absorbing the urine and a feces inlet cutting part receiving the feces.

Further, when the base layer and the skin contact layer are coupled to each other, a portion located on the outer side of the second elastic members and a portion located on the inner side of the first elastic members are coupled.

In addition, a receiving space is formed between the upper end of the base layer where the cover layer is located and the lower end of the skin contact layer.

Further, the second elastic members is located between the inlet cutting part and each of both edges of the skin contact layer.

Advantageous Effects

As described above, according to the present invention, it is possible to maintain a clean and dry state of an inner surface of a diaper in contact with a skin of a wearer and prevent the skin of buttocks of the wearer from being contaminated or damaged.

DETAILED DESCRIPTION

Hereinafter, preferred embodiments of the present invention will be described in detail with reference to the accompanying drawings. The same elements of the drawings are denoted by the same reference symbols whenever possible. Further, the detailed description of publicly-known function and configuration that may make the gist of the present invention unnecessarily ambiguous will be omitted.

Figure 1:
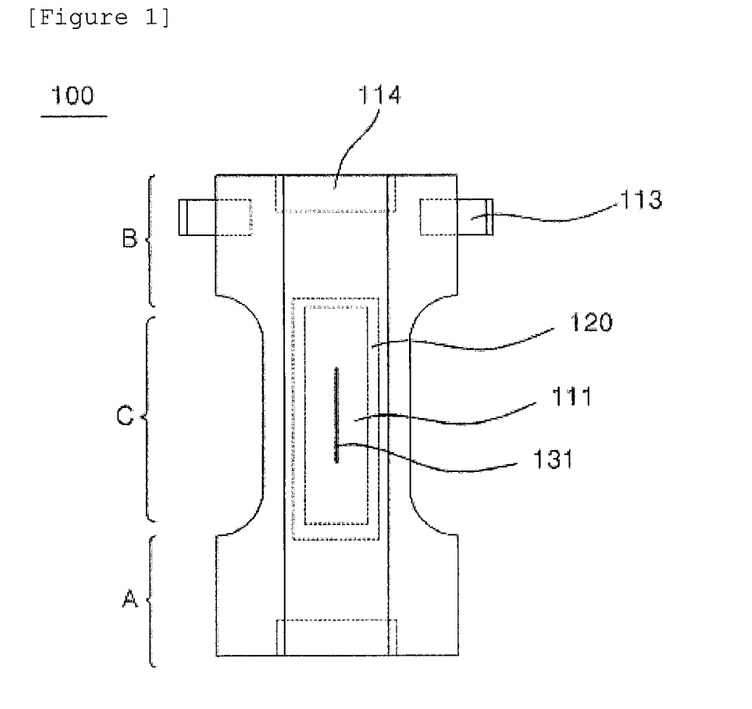
FIG. 1 is a plan view of a disposable diaper according to an embodiment of the present invention.
Figure 2:
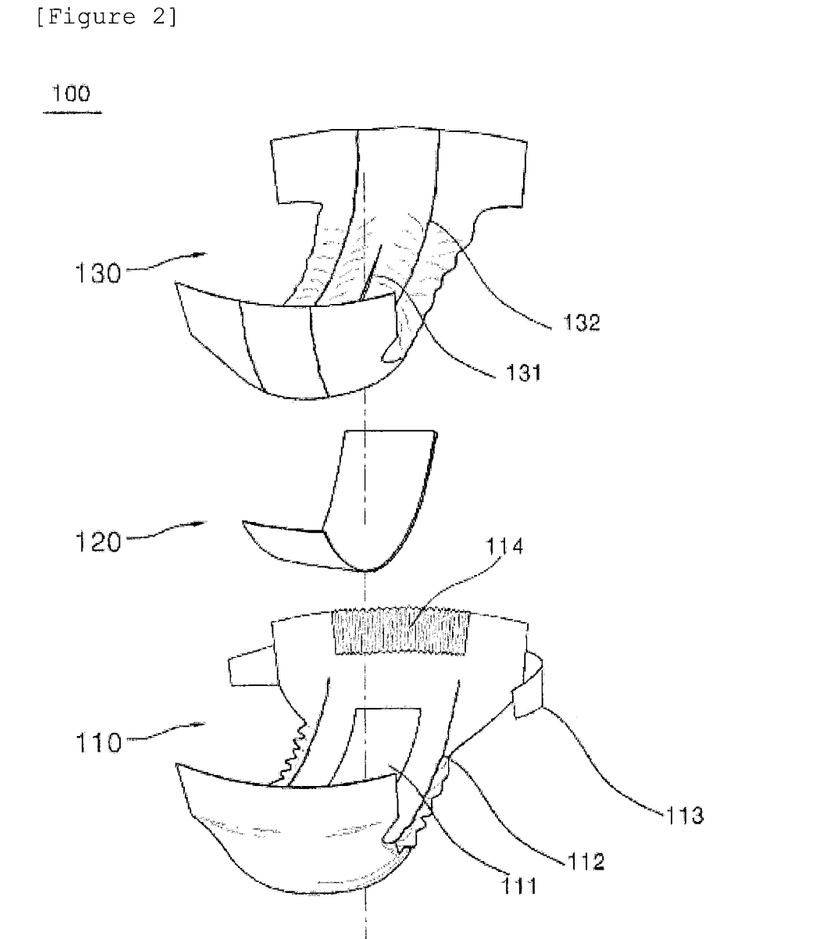
FIG. 2 is an exploded perspective view of the disposable diaper according to the embodiment of the present invention, which is divided into layers.
Figure 3:
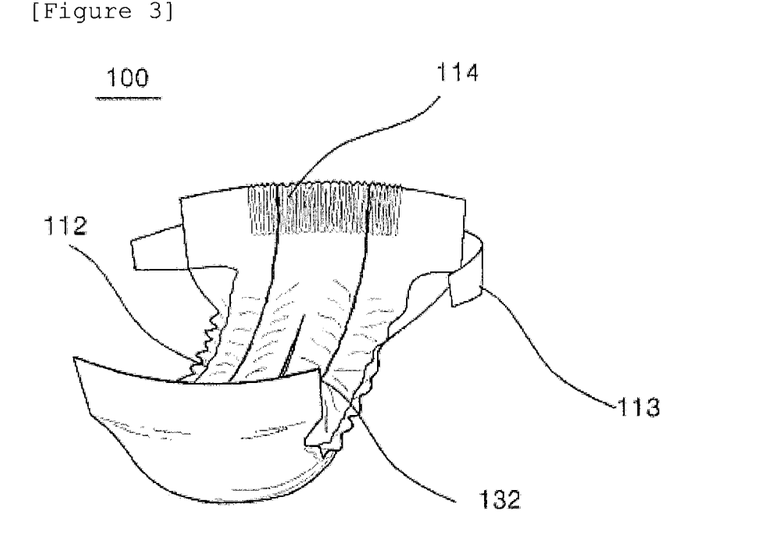
FIG. 3 is a perspective view of the disposable diaper according to the embodiment of the present invention.

FIGS. 1 to 3 are diagrams illustrating a disposable diaper according to an embodiment of the present invention. As illustrated in FIG. 1, when the disposable diaper 100 is divided by body parts, the disposable diaper 100 may be divided into a front surface part A touching an abdomen of a wearer 1, a rear surface part B touching a back of the wearer 1, and a gap part C in which the front surface part A and the rear surface part B extend in the lengthwise direction so as to pass through a space between legs of the wearer 1 and in the present invention, in order to specifically describe a feature, the disposal diaper 100 is divided into layers.

The disposable diaper 100 according to the embodiment of the present invention includes a base layer 110, a cover layer 120, and a skin contact layer 130 as illustrated in FIG. 2 and the base layer 110, the cover layer 120, and the skin contact layer 130 are integrally formed as illustrated in FIG. 3.

An external surface of the base layer 110 is made of a waterproof material so that the base layer 110 prevents urine and feces 10 generated by the wearer 1 from flowing out to the outside. An elastic part 114 is formed in the rear surface part B so as to flexibly surround the waist of the wearer 1 and bonding parts 113 attached to the surface of the waterproof material of the front surface part A are formed on both left and right ends of the rear surface part B.

This is a method that generally wears the disposable diaper 100 and a detailed description thereof will be omitted and in addition to this method, the front surface part A and the rear surface part B are extended and coupled so as to surround the waist of the wearer 1 to be formed in a panty shape.

This is also a method that generally forms the disposal diaper and the detailed description thereof will be omitted.

Further, in the base layer 110, an absorber 111 is provided on an inner surface in the lengthwise direction based on the center of the gap part C and first elastic members 112 are stretchably provided at both sides of the lengthwise direction so as to surround the legs of the wearer 1. In this case, it is preferable that a plurality of first elastic members 112 may be provided according to a degree of elasticity.

Herein, in the description of the base layer 110, the inner surface or the upper end refers to the inside which is the skin side when worn by the wearer 1, and the outer surface or the lower end refers to the outside which does not contact the skin of the wearer 1.

Herein, the absorber 111 is seated and fixed on the inner surface of the base layer 110 and the absorber 111 extends in either direction of the front surface part A or the rear surface part B or in both directions to increase absorption force of the urine.

The cover layer 120 is located on the upper end of the absorber 111 and covers the absorber 111 to prevent the absorber 111 from being released to the outside and the urine of the wearer 1 is easily absorbed in the absorber and the cover layer 120 is preferably made of a material that prevents the absorber 111 from being released to the outside.

The skin contact layer 130 is located on the upper end of the base layer 110 where the cover layer 120 is located and the inlet cutting part 131 which is cut with a predetermined length is formed so that the urine and feces 10 may easily reach the cover layer 120 or the absorber 111, and second elastic members 132 which come in close contact with a lower skin of the buttocks of the wearer 1 is formed in the lengthwise direction of both sides of the inlet cutting part 131.

In this case, the second elastic member 132 is formed on the skin contact layer 130 in the lengthwise direction and preferably formed in parallel to the skin contact layer 130.

Figure 4:
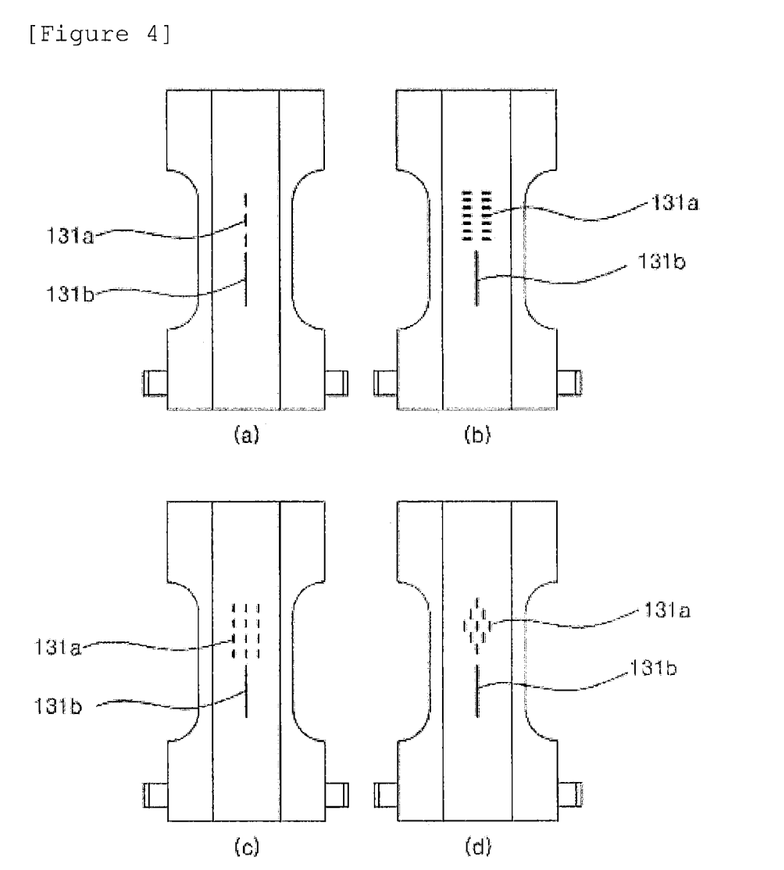
FIG. 4 is a diagram illustrating various embodiments of an inlet cutting part of the disposable diaper according to the embodiment of the present invention.

Further, the inlet cutting part 131 may be separated into a urine inlet cutting part 131a in which the urine is absorbed and a feces inlet cutting part 131b in which the feces 10 is received. A shape of the urine inlet cutting part 131a may be diversified as described in the embodiment illustrated in FIGS. 4(a) to 4(d), but the feces inlet cutting part 131b is preferably formed in a wearing lengthwise direction. As the feces inlet cutting part 131b is formed in the wearing lengthwise direction, the feces is received through the feces inlet cutting part 131b, but when the feces inlet cutting part 131b is circular, the wearer 1 needs to wear the disposal diaper by matching the anus with the circular feces inlet cutting part 131b, and as a result, to match the anus and the feces inlet cutting part 131b, this may be difficult.

Even if the feces inlet cutting part 131b is not formed in an artificially opened form by the formed second elastic member 132, as the second elastic member 132 comes in close contact with the buttocks of the wearer 1, the feces inlet cutting part 131b is opened to both sides of the anus.

The feces inlet cutting part 131b may have all shapes in which the feces inlet cutting part 131b may be elongated in the lengthwise direction of the skin contact layer and may be, for example, linear, rectangular, and elliptical.

This is intended to be worn and maintained in alignment with an exact position of the user's anus and is not limited to one shape.

In addition, even if the urinary tract of the wearer 1 is positioned above the skin contact layer 130, the urine may be easily transferred to the absorber 111 through the urine inlet cutting part 131a.

When the urine inlet cutting part 131a is significantly opened and the urinary track portion of the wearer 1 and the cover layer 120 come into contact with each other, the wearer may feel discomfort due to the absorbed urine, and as a result, it is preferable that the buttocks and the urinary tract portions of the wearer and the cover layer 120 are not in contact with each other.

At least one urine inlet cutting part 131a may be formed and may be formed so that the urine may flow in the lengthwise direction of the skin contact layer 130 or in any direction.

Since the urine inlet cutting part 131a is formed as in the present invention, a speed at which the urine is transferred to the absorber 111 through the urine inlet cutting part 131a is faster than a speed at which the urine passes through a nonwoven fabric and is transferred to the absorber 111 in the related art, and as a result, the skin contact layer 130 may be maintained in a dried state.

In Further, in order to maintain the dried state, it is preferable to use a hydrophobic material rather than a hydrophilic material.

When the hydrophobic material is used, the urine flows over the hydrophobic material to be absorbed by the absorber 111 through the urine inlet cutting part 131a, and the backflow of the urine to the skin contact layer 130 may be reduced.

As another material of the skin contact layer 130, it is preferable to use a skin contact layer 130 made of a natural material made of cotton for a user of which skin is sensitive to synthetic fibers and if necessary, powder for reducing moisture or a material to which a skin moisturizing agent, and a skin care material such as oil or aloe are added may be selectively used.

In order to make the skin contact layer 130 more closely contact with the skin, if the diaper is formed in a state in which an elastic film or the nonwoven fabric which are laminated with the filament and are slightly pulled, the skin contact layer 130 may be brought into closer contact with the skin of the buttocks by elasticity of the material to shrink.

Herein, the portion of the skin contact layer 130 where the urine inlet cutting part 131a is formed may be formed in close contact with the cover layer 120.

Further, a wing layer (not illustrated) having a leakage preventing function may be further formed in the lengthwise of the periphery of the upper end of the skin contact layer 130 so as to prevent the urine and the feces 10 from leaking to a thigh.

Figure 5:
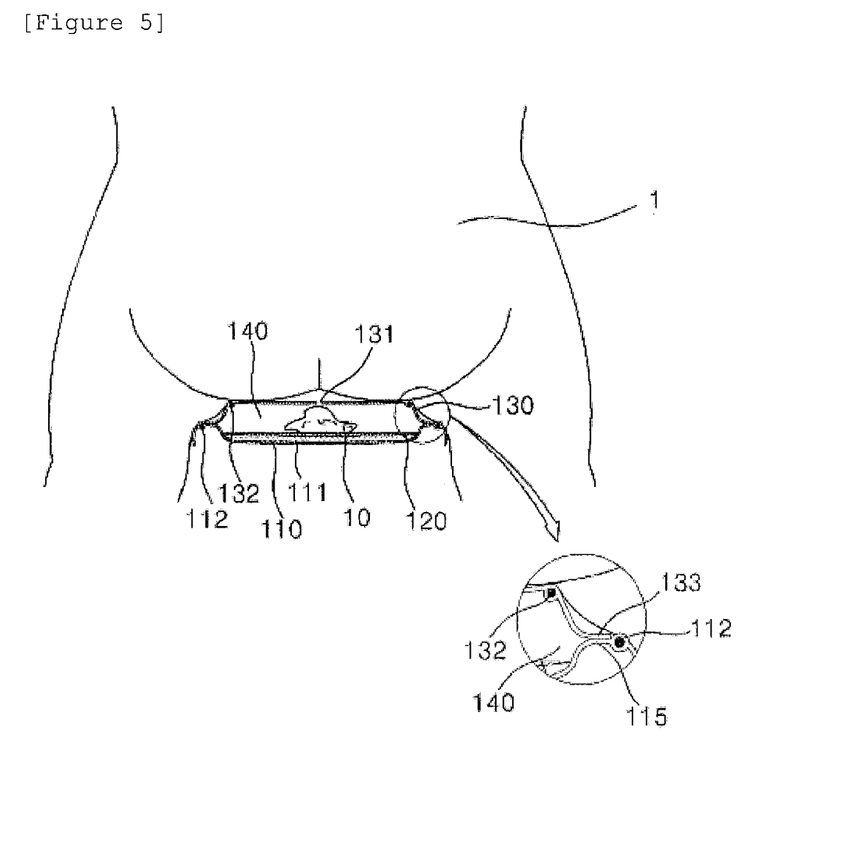
FIG. 5 is a diagram illustrating a wearing state of the disposable diaper according to the embodiment of the present invention.

As illustrated in FIG. 5, when the base layer 110 and the skin contact layer 130 are coupled to each other, a portion located outside the second elastic member 132, that is, an end 133 located at the edge of the skin contact layer 130 and an inner end 115 of the base layer 110 located inside the first elastic member 112 are bonded to couple the base layer 110 and the skin contact layer 130 to each other and while the base layer 110 and the skin contact layer 130 are coupled to each other, the first elastic member 112 of the base layer 110 is preferably located outside the second elastic member 132 of the skin contact layer 130.

Further, the second elastic member 132 is brought into close contact with the buttocks of the wearer 1 and the first elastic member 112 is brought into close contact with the thigh region of the wearer 1 so that a receiving space 140 is formed in the space between the buttocks of the wearer 1 and the thigh, that is, between the upper end of the base layer 110 provided with the first elastic member 112 and the lower end of the skin contact layer 130 provided with the second elastic member 132.

In this case, it is preferable that a plurality of second elastic members 132 may be provided according to the degree of elasticity of the second elastic member 132.

Further, the feces 10 which is introduced through the inlet cutting part 131 may be received by the receiving space 140.

Herein, the receiving space 140 may further include a separation membrane (not illustrated) so that the feces 10 drawn through the feces inlet cutting part 131b is separated without being moved in a direction in which the urine inlet cutting part 131a is formed.

Thus, the present invention has the effect of preventing a feces 10 from touching the vagina and the urinary tract of the female by preventing the feces 10 from moving toward the lower end in which the urine inlet cutting part 131a is formed.

The present invention has the effect of maintaining the inner surface of the diaper, which is in contact with the skin of the wearer, in a clean and dry state and preventing the skin of the buttocks of the wearer from being contaminated or damaged.

The disposable diaper as described above is not limited to the configurations and the operation methods of the embodiments described above. The above embodiments may be configured so that all or some of the embodiments may be selectively combined to make various modifications.

EXPLANATION OF REFERENCE NUMERALS AND SYMBOLS

1: Wearer
10: Feces
100: Disposal diaper
110: Base layer
111: Absorber
112: First elastic member
113: Bonding part
114: Elastic part
115: Inner end
120: Cover layer
130: Skin contact layer
131: Inlet cutting part
131: Urine inlet cutting part
131b: Feces inlet cutting part
132: Second elastic member
133: End
140: Receiving space

The invention claimed is:

1. A disposable diaper integrally formed to have a front surface part configured to touch a wearer's abdomen, a rear surface part configured to touch the wearer's back, and a gap part in which the front surface part and the rear surface part extend in a lengthwise direction so as to be configured to pass between the wearer's legs, which is integrally formed, the disposable diaper comprising:

a base layer including an absorber positioned at an upper end thereof in the lengthwise direction of the gap part, and first elastic members on both sides in the lengthwise direction so as to be configured to come into contact with the wearer's thigh;

a cover layer positioned at an upper end of the absorber so as to cover the absorber; and a skin contact layer positioned at the upper end of the base layer so as to cover the cover layer, the skin contact layer having an inlet cutting part of a predetermined length in a line shape, and second elastic members continuously formed from the front surface part to the rear surface part in the lengthwise direction on both sides and configured to come into close contact with a bottom layer skin of the wearer's buttocks and continuously formed from the front surface part to the rear surface part so that urine and feces easily reach the cover layer or the absorber, wherein when the base layer and the skin contact layer are coupled to each other, a portion located on an outer side of the second elastic members at an edge of the skin contact layer and a portion located on an inner side of the first elastic members at an inner end of the base layer are continuously and directly coupled from the front surface part up to the rear surface part, thereby a receiving space is formed between the upper end of the base layer where the cover layer is located and an lower end of the skin contact layer of the second elastic members.

2. The disposable diaper of claim 1, wherein the inlet cutting part is divided into a urine inlet cutting part in which urine is selectively absorbed only by a necessary portion of the skin contact layer and a feces inlet cutting part in which the feces are received, and an interval between the urine inlet cutting part and the feces inlet cutting part is determined so that the interval for men is long and the interval for women is short to fit into a body structure, or the inlet cutting part is configured to have only the feces inlet cutting part.

3. The disposable diaper of claim 1, wherein the second elastic members are located between the inlet cutting part and each of both edges of the skin contact layer to prevent the feces or the urine from leaking from both sides of the skin contact layer on a top of the skin contact layer before entering the inlet cutting part and guide the feces or the urine to flow into the inlet cutting part at a center.

4. The disposable diaper of claim 1, wherein the receiving space extends laterally between the first and second elastic members.

5. The disposable diaper of claim 1, wherein the skin contact layer extends to the first elastic members.

6. The disposable diaper of claim 3, wherein the skin contact layer is a planar sheet extending at least from the first elastic member to the second elastic member.

7. The disposable diaper of claim 1, wherein the skin contact layer is a planar sheet extending at least from the first elastic member to the second elastic member and further extends from the second elastic member to the inlet cutting part.

8. The disposable diaper of claim 4, wherein the skin contact layer is a planar sheet extending at least from the first elastic member to the second elastic member and from the second elastic member to the inlet cutting part, and the receiving space further extends laterally between the second elastic member and the inlet cutting part.

\* \* \* \* \*